United States Patent
Li et al.

(10) Patent No.: US 11,802,820 B2
(45) Date of Patent: Oct. 31, 2023

(54) METHOD FOR DIGITIZING BONE MARROW SMEAR

(71) Applicant: Hangzhou Zhiwei Information Technology Co., Ltd., Hangzhou (CN)

(72) Inventors: Qiang Li, Hangzhou (CN); Ju Lu, Hangzhou (CN); Shun Li, Hangzhou (CN); Yongtao Liu, Hangzhou (CN); Jiajia Hu, Hangzhou (CN)

(73) Assignee: Hangzhou Zhiwei Information Technology Co., Ltd., Hangzhou (CN)

( * ) Notice: Subject to any disclaimer, the term of this patent is extended or adjusted under 35 U.S.C. 154(b) by 709 days.

(21) Appl. No.: 16/979,499

(22) PCT Filed: May 23, 2019

(86) PCT No.: PCT/CN2019/088157
§ 371 (c)(1),
(2) Date: Sep. 9, 2020

(87) PCT Pub. No.: WO2019/228250
PCT Pub. Date: Dec. 5, 2019

(65) Prior Publication Data
US 2021/0096045 A1    Apr. 1, 2021

(30) Foreign Application Priority Data
May 28, 2018  (CN) .......... 201810522618.2

(51) Int. Cl.
G01N 1/00   (2006.01)
G01N 1/28   (2006.01)
G02B 21/36  (2006.01)
C12N 5/077  (2010.01)

(52) U.S. Cl.
CPC .......... *G01N 1/2813* (2013.01); *G02B 21/36* (2013.01); *C12N 5/0669* (2013.01)

(58) Field of Classification Search
CPC .... C12N 5/0669; G02B 21/36; G01N 1/2813; G01N 1/28
See application file for complete search history.

(56) References Cited

U.S. PATENT DOCUMENTS

2013/0020175 A1*  1/2013  McKeen .................. G01N 1/31
                                                      198/346.1

* cited by examiner

*Primary Examiner* — Jyoti Nagpaul
(74) *Attorney, Agent, or Firm* — Yong Chen; Lin Sun-Hoffman; Liu Chen & Hoffman LLP

(57) ABSTRACT

A method includes: obtaining relevant information of the bone marrow smear; generating a global image; generating a to-be-digitized region, an amount of nucleated cells to be collected, and an amount of megakaryocytes to be classified; digitally labeling the bone marrow smear; scanning the to-be-digitized region by low magnification, labeling and identifying a target observation object; generating a switched image of the scanned region; scanning megakaryocytes by low magnification, and labeling and identifying the scanned megakaryocytes, the amount of the scanned megakaryocytes being the same as the amount of megakaryocytes to be classified; generating images of the scanned megakaryocytes; scanning nucleated cells by oil mirror scanning, and labeling and identifying the scanned nucleated cells, the amount of the scanned nucleated cells being the same as the amount of nucleated cells to be collected; generating images of the scanned nucleated cells; and generating a digital smear of the bone marrow smear.

2 Claims, No Drawings

METHOD FOR DIGITIZING BONE MARROW SMEAR

CROSS-REFERENCE TO RELATED APPLICATIONS

This application is based on and claims the priority of Chinese Patent Application No. 201810522618.2, filed on May 28, 2018, which is incorporated herein by reference in its entirety.

TECHNICAL FIELD

The invention belongs to the field of computer medical bone marrow smear examination and, more particularly, to a method of digitizing bone marrow smear.

BACKGROUND

Morphological microscopy of bone marrow cells is one of the key diagnostic tools in hematology, and is commonly used to diagnose a variety of conditions, including leukemia, multiple myeloma, lymphoma, anemia, and whole blood cell reduction. According to "Guidelines for the Diagnosis of Marrow Malignancies" issued by the World Health Organization, detailed and accurate manual microscopic examinations are required for diagnosis. Normal bone marrow contains all differentiated cells at various developmental stages, from early precursor stem cells to functionally mature cells, including hematopoietic stem cells that are the precursors of most blood cells, as well as mesenchymal stem cells and endothelial stem cells that are considered to be gatekeeper cells of the bone marrow. The morphological characteristics of these cells depend on the smear, staining, and image acquisition process. For certain diseases, atypical cell counts can be accurately assessed by some of the more specific immune or molecular markers that have been discovered. However, these markers are not suitable for all diseases. At present, manual microscopic examination is still the primary or only method for monitoring the diagnostic and therapeutic effects. The main drawbacks of the manual microscopic examination are described below.

(1) The work efficiency is low. Traditional microscopic examination requires a hematologist/pathologist to manually inspect the specimen under the microscope for diagnosis. Starting from receiving a stained smear of a specimen, the following processes are required: 1. reading the inspection application form and confirming the patient's information, clinical contents, and the required examination items; 2. visually inspecting the smear specimen and selecting the smear that is relatively satisfactory for staining and pushing; 3. inspecting the smear at low magnification, counting the number of megakaryocytes in the entire smear, evaluating the cell proliferation, and determining whether there are diluted or abnormal cells; 4. inspecting the smear by oil mirror, selecting an area with uniform distribution of cells around a bone marrow granule, and using a bow-shaped or sacral shape moving method to count 200 nucleated cells and 25 megakaryocytes, recording the results on a paper-based nucleated cell classification table or a cell counter while inspecting and classifying; 5 making a morphological diagnosis, inference, or interpretation of the specimen based on the results of the microscopic examination, clinical information, and other examination results; 6. entering the classification results and inspection results into a reporting system and print a paper report. At present, the reporting period of bone marrow examination is still too long, usually around 3 working days. In some hospitals, it may even take a week to provide a report. The long reporting period is not suitable for the responsiveness of modern medicine. Long-term observation in manual microscopic examination is also likely to cause fatigue of the eye and cervical vertebrae of the morphological examiner.

(2) Strong work experience is required. Morphology is typically a strong empirical medicine. It is difficult to make high-quality inspection reports without long-term work experience accumulation and technical proficiency. Professional morphological skills are accompanied by continuous learning, practicing, and re-learning, as well as blending with basic medicine and clinical medicine. Morphological grasp and its significance judgment is a complicated and cumbersome process, which may often requires some flexibility and particularity. Sometimes, even if the cell number and morphology are the same or similar, the results may be different in view of different clinical and other results. The descriptions in the medical textbooks are basic, very typical cell morphology, often focusing on the meaning of teaching and lack of universality. In practice, in different specimen of different patients, different smears thickness, different regions, and different staining, the variance in cell size and shape is large. Therefore, the training of qualified hematologists/pathologists is also a long and boring process. Coupled with the influence of other factors, many hospitals have experienced the loss of morphological examiners.

(3) The standard of microscopic examination is not uniform. At present, the traditional bone marrow cell morphology diagnosis in China mainly relies on bone marrow smear manual microscopic examination. Although blood films have been advocated, they are often overlooked or neglected. Other inspection methods are often divided into different departments or departments, almost all of which are single projects and the intrinsic link between these inspection methods are neglected. Some of the weak blood cell testing departments have relaxed the examination and diagnosis of blood cell morphology under the influence of the specific environment of the automated blood cell analyzer, which has affected the development of blood morphology and the improvement of the overall diagnostic level. In the 2008 Guidelines for Standardization of Bone Marrow Specimens and Reports reported by the ICSH, it is emphasized that a complete morphological diagnosis often requires a comprehensive examination of bone marrow smears and blood films (including cytochemical staining). Through comprehensive examination, several related inspection methods can be reasonably complemented and integrated to promote the overall development of blood morphology.

SUMMARY

The technical problem to be solved by the embodiments of the present disclosure is to provide a method for digitizing a bone marrow smear, which converts a bone marrow physical smear into a digital smear. As a result, the process of manual microscopic examination may be simplified; the consistency and standardization of bone marrow examination report results may be improved; remote consultation may be facilitated; the turnaround time of physical smear, especially special samples, may be reduced; continuous education may be provided for all employees, thus improving bone marrow morphology experience.

In order to solve the above technical problem, an embodiment of the present disclosure provides a method for digitizing a bone marrow smear. The method includes the following steps:

(1) obtaining medical record information related to a bone marrow physical smear;
(2) generating a global image of the bone marrow physical smear;
(3) generating a to-be-digitized region of the bone marrow physical smear, an amount of nucleated cells to be collected, and an amount of megakaryocytes to be classified;
(4) generating a digital label of the bone marrow physical smear;
(5) printing and pasting the digital label on a specific area of the bone marrow physical smear that corresponds to the digital label;
(6) repeating steps (1) to (5) until all digital labels of the bone marrow physical smear are generated and pasted;
(7) loading the bone marrow physical smear with the digital labels into a slide box;
(8) loading the slide box into an entrance of a bone marrow cell scanning device;
(9) transferring the slide box to a loading position of the scanning device;
(10) confirming and recording a position of the bone marrow physical smear in the slide box through infrared scanning the structure of the slide box;
(11) transferring the bone marrow physical smear from the slide box to a stage of the bone marrow cell scanning device;
(12) reading the digital label of the bone marrow physical smear;
(13) switching the bone marrow cell scanning device to low magnification to scan the to-be-digitized region generated in step (3), and identifying and labeling a target observation object in the to-be-digitized region.
(14) generating a stitched image of the region scanned in step (13);
(15) switching the bone marrow cell scanning device to high magnification to scan megakaryocytes, and labeling and identifying the scanned megakaryocytes, the amount of the scanned megakaryocytes being the same as the amount of megakaryocytes to be classified generated in step (3);
(16) generating images of the megakaryocytes scanned in step (15);
(17) adding special mirror oil to the bone marrow physical smear;
(18) switching the bone marrow cell scanning device to oil mirror to scan nucleated cells in the to-be-digitized region, and labelling and identifying the scanned nucleated cells, the amount of the scanned nucleated cells being the same as the amount of nucleated cells to be collected generated in step (3);
(19) generating images of the nucleated cell scanned in step (18);
(20) generating a digital smear of the bone marrow physical smear;
(21) transferring the bone marrow physical smear from the stage to the slide box;
(22) repeating steps (11) to (22) until all of the bone marrow physical smears are scanned to generate digital smears;
(23) transferring the slide box from the loading position to the entrance of the scanning device; and
(24) taking out the slide box, and complete the entire process of digitizing the bone marrow smear.
In an embodiment, the specific area in the step (5) is a label area of a slide, wherein the slide is divided into a label area and a detection area along a lateral scale line.

The embodiments of the present disclosure have the advantages of converting the bone marrow physical smear into a digital smear, simplifying the process of manual microscopic examination, improving the consistency and standardization of the results of a bone marrow examination report, facilitating remote consultation, reducing the turn-around time of the physical smear, especially for special sample, and providing continuing education for all employees to improve bone marrow morphological experience.

DETAILED DESCRIPTION

The invention can be better understood in light of the following examples. However, those skilled in the art will understand that the description of the embodiments is merely illustrative of the invention and should not be construed as limiting.

According to an embodiment, a method for digitizing a bone marrow smear includes the following steps.

In step (1), medical record information related to a bone marrow physical smear is obtained.

In step (2), a global image of the bone marrow physical smear is generated.

In step (3), a to-be-digitized region of the bone marrow physical smear is generated, and an amount of nucleated cells to be collected and an amount of megakaryocytes to be classified are generated.

In step (4), a digital label of the bone marrow physical smear is generated.

In step (5), the digital label is printed and pasted on a label area of the bone marrow physical smear that corresponds to the digital label.

In step (6), steps (1) to (5) are repeated until all digital labels of the bone marrow physical smear are generated and pasted.

In step (7), the bone marrow physical smear with the digital labels is loaded into a slide box.

In step (8), the slide box is loaded into an entrance of a bone marrow cell scanning device.

In step (9), the slide box is transferred to a loading position of the scanning device.

In step (10), a position of the bone marrow physical smear in the slide box is confirmed and recorded through infrared scanning the structure of the slide box.

In step (11), the bone marrow physical smear is transferred from the slide box to a stage of the bone marrow cell scanning device.

In step (12), the digital label of the bone marrow physical smear is read.

In step (13), the bone marrow cell scanning device is switched to low magnification to scan the to-be-digitized region generated in step (3), and a target observation object in the to-be-digitized region is identified and labelled.

In step (14), a stitched image of the region scanned in step (13) is generated.

In step (15), the bone marrow cell scanning device is switched to high magnification to scan megakaryocytes, the amount of the scanned megakaryocytes being the same as the amount of megakaryocytes to be classified generated in step (3). The scanned megakaryocytes are labelled and identified.

In step (16), images of the megakaryocytes scanned in step (15) are generated.

In step (17), special mirror oil is added to the bone marrow physical smear.

In step (18), the bone marrow cell scanning device is switched to oil mirror to scan nucleated cells in the to-bedigitized region, the amount of the scanned nucleated cells being the same as the amount of nucleated cells to be collected generated in step (3). The scanned nucleated cells are labelled and identified.

In step (19), images of the nucleated cells scanned in step (18) are generated.

In step (20), a digital smear of the bone marrow physical smear is generated.

In step (21), the bone marrow physical smear is transferred from the stage to the slide box.

In step (22), steps (11) to (22) are repeated until all of the bone marrow physical smears in the slide box are scanned to generate digital smears.

In step (23), the slide box is transferred from the loading position to the entrance of the scanning device.

In step (24), the slide cassette was taken out, and the entire process of digitizing the bone marrow smear is completed.

The embodiments of the present disclosure have the advantages of converting the bone marrow physical smear into a digital smear, simplifying the process of manual microscopic examination, improving the consistency and standardization of the results of a bone marrow examination report, facilitating remote consultation, reducing the turn-around time of the physical smear, especially for special sample, and providing continuing education for all employees to improve bone marrow morphological experience.

Other embodiments of the disclosure will be apparent to those skilled in the art from consideration of the specification and practice of the disclosure disclosed here. This application is intended to cover any variations, uses, or adaptations of the disclosure following the general principles thereof and including such departures from the present disclosure as come within known or customary practice in the art. It is intended that the specification and examples be considered as exemplary only, with a true scope and spirit of the disclosure being indicated by the following claims.

It is to be understood that the present disclosure is not limited to the exact construction that has been described above, and that various modifications and changes can be made without departing form the scope thereof. It is intended that the scope of the disclosure only be limited by the appended claims.

What is claimed is:

1. A method for digitizing a bone marrow smear, comprising the steps of:
    (1) obtaining medical record information related to a bone marrow physical smear;
    (2) generating a global image of the bone marrow physical smear;
    (3) generating a to-be-digitized region of the bone marrow physical smear, an amount of nucleated cells to be collected, and an amount of megakaryocytes to be classified;
    (4) generating a digital label of the bone marrow physical smear;
    (5) printing and pasting the digital label on a specific area of the bone marrow physical smear that corresponds to the digital label;
    (6) repeating steps (1) to (5) until all digital labels of the bone marrow physical smear are generated and pasted;
    (7) loading the bone marrow physical smear with the digital label into a slide box;
    (8) loading the slide box into an entrance of a bone marrow cell scanning device;
    (9) transferring the slide box to a loading position of the bone marrow cell scanning device;
    (10) confirming and recording a position of the bone marrow physical smear in the slide box through infrared scanning the structure of the slide box;
    (11) transferring the bone marrow physical smear from the slide box to a stage of the bone marrow cell scanning device;
    (12) reading the digital label of the bone marrow physical smear;
    (13) switching the bone marrow cell scanning device to low magnification to scan the to-be-digitized region generated in step (3), and labeling and identifying a target observation object in the to-be-digitized region;
    (14) generating a stitched image of the region scanned in step (13);
    (15) switching the bone marrow cell scanning device to high magnification to scan megakaryocytes, and labeling and identifying the scanned megakaryocytes, the amount of the scanned megakaryocytes being the same as the amount of megakaryocytes to be classified generated in step (3);
    (16) generating images of the megakaryocytes scanned in step (15);
    (17) adding special mirror oil to the bone marrow physical smear;
    (18) switching the bone marrow cell scanning device to oil mirror to scan nucleated cells, and labeling and identifying the scanned nucleated cells, the amount of the scanned nucleated cells being the same as the amount of nucleated cells to be collected generated in step (3);
    (19) generating images of the nucleated cells scanned in step (18);
    (20) generating a digital smear of the bone marrow physical smear;
    (21) transferring the bone marrow physical smear from the stage to the slide box;
    (22) repeating steps (11) to (22) until all of bone marrow physical smears in the slide box are scanned to generate digital smears;
    (23) transferring the slide box from the loading position to the entrance of the bone marrow cell scanning device; and
    (24) taking out the slide box.

2. The method according to claim 1, wherein the specific area in step (5) is a label area of a slide, the slide being divided into a label area and a detection area along a lateral scale line.

* * * * *